United States Patent
Keller et al.

(10) Patent No.: US 10,660,774 B2
(45) Date of Patent: May 26, 2020

(54) DELIVERY CATHETER AND CATHETER ARRANGEMENT

(71) Applicant: BIOTRONIK AG, Buelach (CH)

(72) Inventors: Mark Keller, Aarau (CH); Markus Hepke, Zurich (CH)

(73) Assignee: BIOTRONIK AG, Buelach (CH)

( * ) Notice: Subject to any disclaimer, the term of this patent is extended or adjusted under 35 U.S.C. 154(b) by 215 days.

(21) Appl. No.: 15/628,325

(22) Filed: Jun. 20, 2017

(65) Prior Publication Data

US 2018/0116844 A1 May 3, 2018

(30) Foreign Application Priority Data

Jun. 21, 2016 (DE) .......................... 10 2016 111 323

(51) Int. Cl.
*A61F 2/966* (2013.01)
*A61F 2/954* (2013.01)
(Continued)

(52) U.S. Cl.
CPC ............ *A61F 2/966* (2013.01); *A61F 2/2436* (2013.01); *A61F 2/954* (2013.01); *A61F 2/07* (2013.01);
(Continued)

(58) Field of Classification Search
CPC ........ A61F 2/966; A61F 2/954; A61F 2/2436; A61F 2250/0039; A61F 2002/9665; A61M 25/0074
See application file for complete search history.

(56) References Cited

U.S. PATENT DOCUMENTS 9,554,904 B2 * 1/2017 Gallagher ............. A61F 2/2436
10,010,418 B2 * 7/2018 Marchand ............. A61F 2/2433
(Continued)

FOREIGN PATENT DOCUMENTS

DE 69635676 T2 10/2006
DE 69635676 T2 12/2006
(Continued)

OTHER PUBLICATIONS

Fritzsche-Henke, Martina, et al., "German Search Report" German Patent Application No. DE 10 2016 111 323.9, dated Mar. 1, 2017, 12 pages.
(Continued)

*Primary Examiner* — Julian W Woo
(74) *Attorney, Agent, or Firm* — Greer, Burns & Crain, Ltd; Steven P. Fallon

(57) ABSTRACT

A delivery catheter includes an inner shaft having an atraumatic distal catheter tip. The inner shaft is configured to carry the implant thereon. The catheter tip includes a region that is fixed to the inner shaft and a region that is deformable and not fixed to the inner shaft. An outer shaft surrounds the inner shaft and is displaceable relative thereto. An implant capsule at a distal end of the outer shaft is configured to encase the implant and to release the implant at the target site via relative displacement of the inner and outer shafts. A plunger is axially displaceable with respect to the catheter tip in response to movement of the outer shaft to apply axial compressive force to the catheter tip and deform the region that is deformable and expand that region radially.

17 Claims, 2 Drawing Sheets

(51) Int. Cl.
*A61F 2/95* (2013.01)
*A61F 2/24* (2006.01)
A61M 25/00 (2006.01)
A61F 2/07 (2013.01)
A61F 2/06 (2013.01)

(52) U.S. Cl.
CPC . *A61F 2002/061* (2013.01); *A61F 2002/9665* (2013.01); *A61F 2250/0039* (2013.01); *A61M 25/0074* (2013.01)

(56) References Cited

U.S. PATENT DOCUMENTS

| | | |
|---|---|---|
| 2008/0255652 A1* | 10/2008 | Thomas .................. A61F 2/95 623/1.11 |
| 2009/0264859 A1 | 10/2009 | Mas |
| 2013/0079872 A1 | 3/2013 | Gallagher |
| 2014/0200649 A1 | 7/2014 | Essinger et al. |

FOREIGN PATENT DOCUMENTS

| | | |
|---|---|---|
| WO | 2012009006 A1 | 1/2012 |
| WO | 2012023981 A2 | 2/2012 |

OTHER PUBLICATIONS

Melanie Geuer, European Search Report for Application No. 17176863.3, dated Nov. 10, 2017.

* cited by examiner

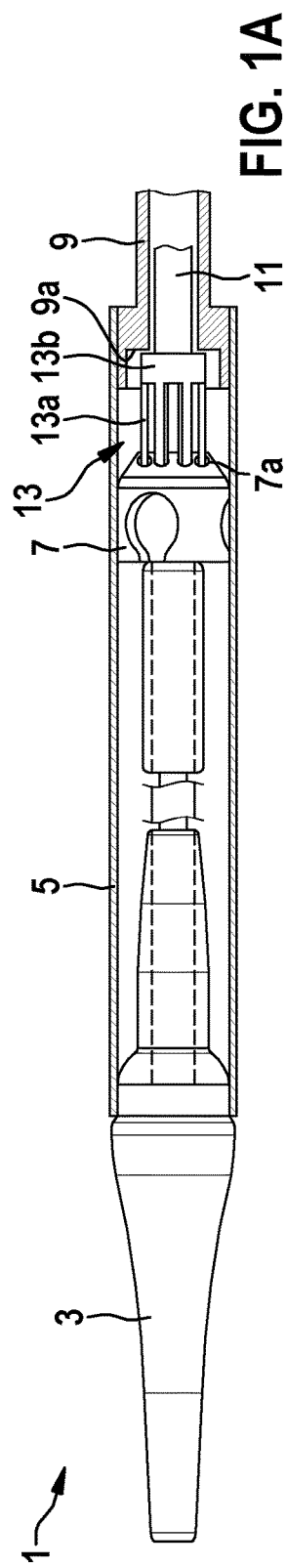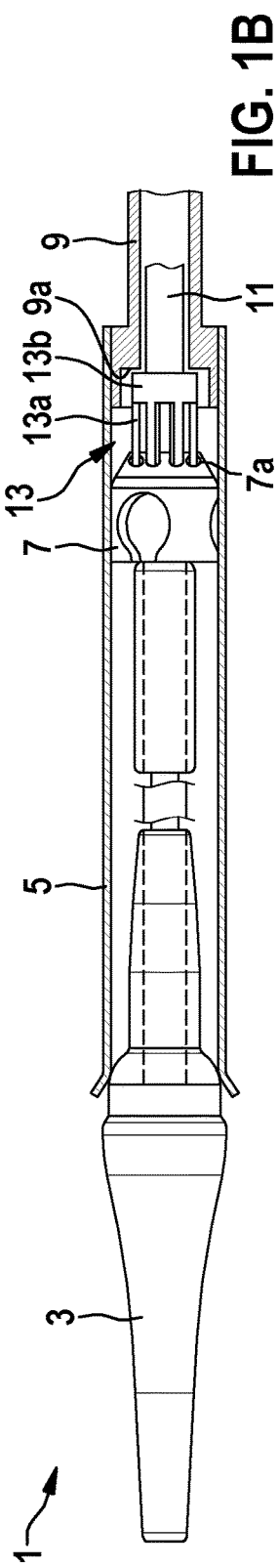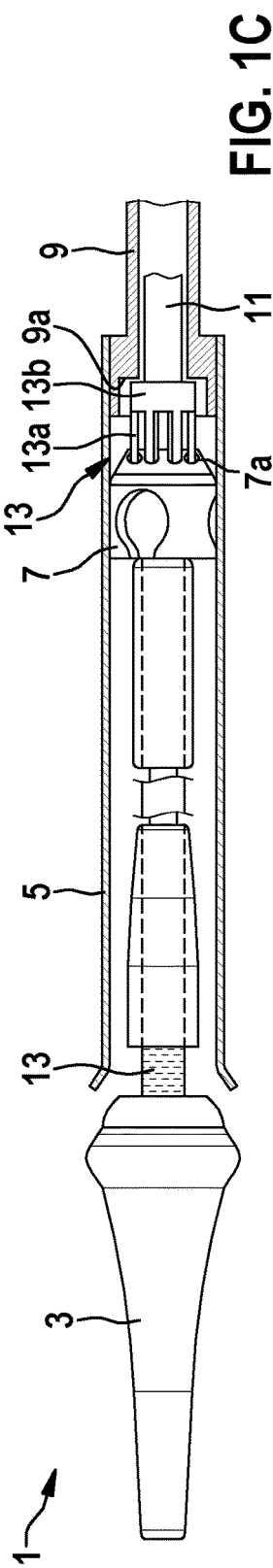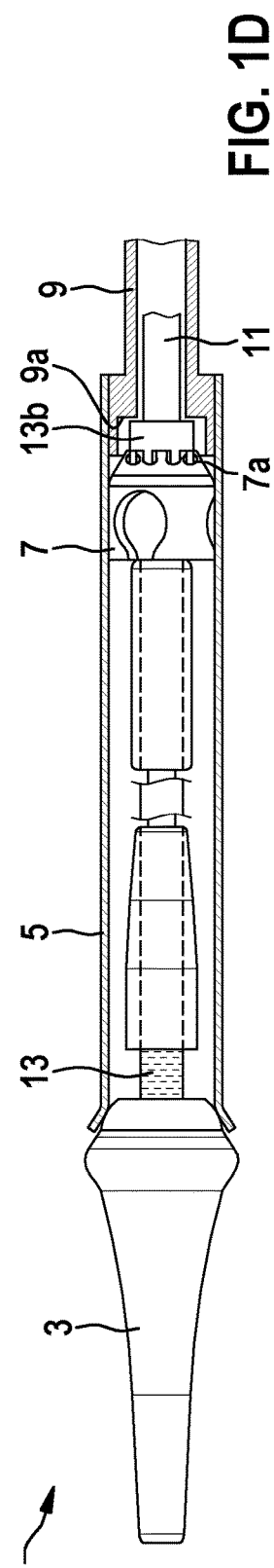

DELIVERY CATHETER AND CATHETER ARRANGEMENT

PRIORITY CLAIM

This application claims priority under 35 U.S.C. § 119 and all applicable statutes and treaties from prior German Application DE 10 2016 111 323.9, filed Jun. 21, 2016.

FIELD OF THE INVENTION

A field of the invention is delivery catheters for minimally invasive delivery of implants, including stents and heart valve prostheses.

BACKGROUND

Minimally invasive surgical interventions have gained steadily in importance for years and are indispensable for example for the treatment of stenoses. Recently, they have also been used increasingly in the implantation of artificial heart valves. Suitable delivery catheters are known in a very wide range of designs and are the subject of on-going further development. In recent years, the development has focused particular attention on catheters which not only permit the initial placement, but also the removal or positioning of cardiovascular implants.

Delivery catheters of this type typically consist fundamentally of a first, inner catheter shaft, at the distal end of which there is arranged the implant. The implant and the first, inner catheter shaft are surrounded by a second, outer catheter shaft. The distal region of the second outer catheter shaft, which surrounds the implant, is often referred to as an implant capsule, or occasionally as a catheter sleeve. The implant capsule can consist of the same material as the second outer catheter shaft or of another material connected to the second outer catheter shaft. "Proximal" denotes a part of the delivery catheter disposed closer to the operating surgeon, and "distal" accordingly denotes a part of the delivery catheter disposed further away from the operating surgeon.

The implants are often constructed using a shape-memory material. In these cases, the implants are held in their compressed form by the catheter sleeve surrounding them as they are delivered to the site of implantation. By displacing the catheter sleeve, for example proximally, the retaining force exerted onto the implant by the catheter sleeve disappears and the implant expands.

Recently, solutions have been proposed to permit a return (resheathing) of an already released implant into the delivery catheter, i.e. especially into the implant capsule. Such solutions are very much welcomed by the operating surgeons because they permit corrections during the delivery process and thus help the implantation process to be concluded with the best-possible result. Especially with retraction of heart valve stents into the implant capsule, or, more specifically, as the distal catheter end is drawn back over the stent, relatively high reaction forces occur. These forces and stresses lead to complex problems, as described by way of example in the prior art description in US 2011/0098804 A1, and are linked to the search for a (partial) solution.

It is known to produce the catheter tip from a soft/ atraumatic material to avoid injuries to the vessel walls as the catheter device is advanced. The soft material is intended to afford sufficient protection of the sensitive vessel inner wall and the natural aortic valve when an aortic valve replacement catheter is passed therethrough. In the event of very sharp bends of the transition region between distal catheter tip and adjoining outer tube (capsule containing the implant), it can be that edges are exposed which might injure the vessel inner wall or the natural aortic valve. Particularly in systems of the above-mentioned type which can recapture a partially released implant, the catheter components are heavily loaded, which can lead to an even more pronounced edge formation. The reason for this pronounced edge formation is the funnel-shaped expansion of the capsule by the return by way of the partially released implant. There is an enlarged peripheral edge at the distal catheter end.

SUMMARY OF THE INVENTION

The invention provides a delivery catheter and a corresponding catheter arrangement which largely rule out injury to the vessel inner wall or the natural aortic valve during use, more specifically during or after a resheathing. A preferred embodiment delivery catheter includes an inner shaft having an atraumatic distal catheter tip. The inner shaft is configured to carry the implant thereon. The catheter tip includes a region that is fixed to the inner shaft and a region that is deformable and not fixed to the inner shaft. An outer shaft surrounds the inner shaft and is displaceable relative thereto. An implant capsule at a distal end of the outer shaft is configured to encase the implant and to release the implant at the target site via relative displacement of the inner and outer shafts. A plunger is axially displaceable with respect to the catheter tip in response to movement of the outer shaft to apply axial compressive force to the catheter tip and deform the region that is deformable and expand that region radially.

BRIEF DESCRIPTION OF THE DRAWINGS

Advantages and expedient features of the invention will also become clear from the following description of an exemplary embodiment provided with reference to the figures, in which:

FIG. 1A to 1D show illustrations of the distal end region of an embodiment of the delivery catheter according to the invention in the form of a longitudinal sectional illustration, in various phases of use.

DETAILED DESCRIPTION OF THE PREFERRED EMBODIMENTS

Figure 2A:
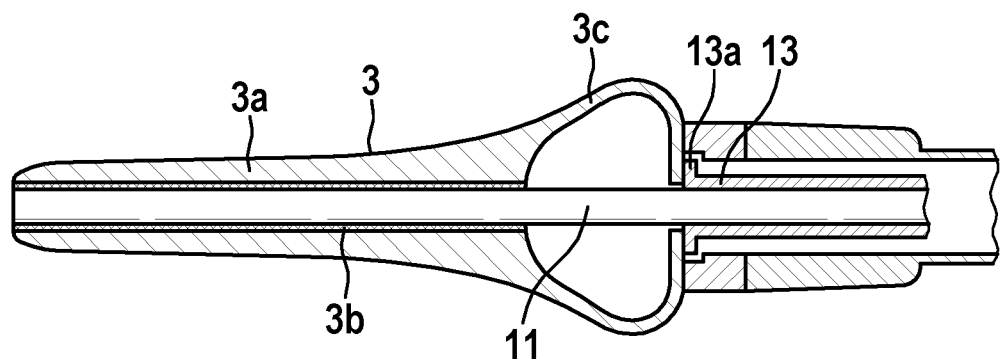
FIGS. 2A and 2B show further enlarged detailed views of the catheter tip and of the distal part of the plunger in two variants of the embodiment shown in FIG. 1A to 1D.

The invention relates to a delivery catheter for inserting an implant at a target site in a vessel or organ of a mammal, wherein the delivery catheter has an inner shaft, which is designed to carry the implant during the insertion and to release the implant at the target site and which has an atraumatic distal catheter tip, and an outer shaft, which surrounds the inner shaft and is displaceable relative thereto, for displacing the implant at the target site, wherein the outer shaft, at its distal end, carries an implant capsule for receiving the implant in an encasing manner during the insertion.

Preferred embodiment delivery catheters provide, at the distal end of the implant capsule, a temporarily effective protection element or a "buffer" of sufficiently great radial extent to avoid the dangerous exposure of the end of the implant capsule over the catheter tip of the delivery catheter depending on the situation. Preferred embodiments provide a temporary enlargement of the radial extent of the soft catheter tip. This temporary enlargement of the tip radius by is via a plunger that implements its effect in specific situations of use, but within the scope of conventional handling and without complicating the operating procedure for the operating surgeon. The plunger is responsive to movement of the outer shaft as it is moved forward relative to the inner shaft beyond a predetermined point, and acts on the catheter tip by applying the axially acting compressive force. The plunger transfers this compressive force to the proximal end of the catheter tip, whereby the resilient expansion thereof is implemented.

Because the atraumatic catheter tip, in the expanded state, has a larger diameter than the expanded distal end of the implant capsule, the risk of an exposed edge at which the implant capsule could become hooked on deposits or anatomical structures in the vessel or heart of the patient, thus causing injury, is eliminated. As a result of this solution, there is a lower risk of the detachment of deposits (plaque) and of injury to anatomical structures, such as vessel inner wall and natural aortic valve, by the catheter system during the aortic valve implantation. This solution thus reduces the likelihood of an embolism. This solution further promotes a simpler re-crossing of the native valve, since the system can no longer become caught by the exposed edges of the distally expanded capsule.

The handling of the delivery catheter according to the invention, under consideration of characteristic design aspects thereof, can be described as follows:

In order to recapture the partially released prosthesis, the implant capsule is moved distally. The capsule is secured to the outer shaft of the catheter. This outer shaft is driven and moved forward (distally) by way of the movable part of the handle. This outer shaft in turn contacts the plunger during the resheathing process from a specific point (overstroke). The plunger is designed such that it is guided through the prosthesis connector. It is also arranged such that it is not hindered in terms of its axial movement by the crimped-on prosthesis.

This plunger is now moved toward the atraumatic catheter tip after the resheathing and is pressed against the catheter tip. The axial pressure of the plunger on the tip causes the tip to be resiliently expanded or deformed in the radial direction. This expansion in the radial direction is achieved in that the tip, at its distal end, is rigidly connected to the inner shaft of the catheter. If the tip is acted on by axial pressure, it is axially compressed and thus enlarges in the radial direction.

During the repeated release process of the prosthesis, the tip is returned again to its original form, since the compressive stress no longer acts thereon and the restoring forces cause it to relax again axially and radially.

The present invention is particular useful, if the implant is design as heart valve prosthesis. The heart valve prosthesis comprises a self-expanding frame (stent) and a thereto fastened valve. The self-expanding frame is equipped to be attached to an implant connector at the inner shaft. Thereby the prosthesis is axially fixed until the implant capsule is completely removed.

The plunger is preferably connected to a suitable actuation element, preferably to the handle of the catheter, which is moved out through a predefined point after the resheathing and triggers the movement of the plunger towards the catheter tip.

In a preferred embodiment of the invention the catheter tip is formed as a soft-resilient moulded plastics part, at least in the expandable proximal portion. A totally soft-elastic embodiment of the catheter tip, i.e. over the entire length, is more preferred; however, a certain rigidity is provided in any case in the distal region by the distal fixed connection to the inner shaft.

In a further embodiment the catheter tip is not fixed to the inner shaft at the proximal end, but can be slid relative to the inner shaft when expanded. In principle, this feature is not necessary for the execution of the invention; the expansion of the catheter tip according to the invention can also be achieved in principle if the proximal end of the catheter tip is fixed. However, the displaceability offers advantageous possibilities for implementing the expansion.

In conjunction herewith, an embodiment is provided in which a plain bushing, which increases the slidability relative to the inner shaft and improves the transfer of force from the plunger to the proximal end of the catheter tip, is inserted into the proximal end of the catheter tip. An additional element of this type at the catheter tip, which itself is preferably made of a slightly harder plastic than the tip, indeed somewhat complicates the manufacture of the insertion catheter, but improves the functionality.

A further optimization of the functionality is achieved in that the catheter tip is connected over the greater part of its longitudinal extent at its entire inner periphery to the outer periphery of the inner shaft in an integrally bonded manner, in particular is glued or welded. This measure on the one hand increases stability and on the other hand serves to avoid uncontrolled deformations over the course of the length of the tip. In accordance with the tests performed by the inventors, it is expedient if the diameter of the catheter tip, at the proximal end in the unexpanded state, is substantially equal to the diameter of the implant capsule and if the greatest diameter of the catheter tip in the expanded state lies in a range between 1.05 times and 1.4 times, in particular 1.1 times and 1.35 times, particularly preferably 1.25 times and 1.3 times, the diameter of the implant capsule. This ensures, in all critical situations of use, a sufficient protection of the adjacent vessel walls from the expanded distal end of the implant capsule.

In a further embodiment of the invention the plunger is formed as a spirally cut metal tube in its distal region, at the distal end of which there is formed a ring flange for enlarging the area of contact with the catheter tip. This embodiment on the one hand ensures the necessary compressive rigidity of the plunger, such that it can carry out its function reliably, and on the other hand provides the required bendability in order to maintain flexibility of the delivery catheter when passed through tightly curved vessel portions.

Similarly to known designs of the delivery catheter, an implant connector is fixedly attached to the inner shaft of the implant capsule in a further embodiment. This implant connector here has guide for guiding the plunger during the axial displacement thereof. In a development of this embodiment the guide at the implant connector are formed as through-holes or guide channels through the wall of the implant connector. The plunger is cut in a strip-like manner in its proximal region, in such a way that the strips of the plunger are threaded through the through-holes of the implant connector. The strips of the plunger are gripped at the proximal end thereof in a connection ring, which defines a peripherally closed proximal end of the plunger.

In a further embodiment, the outer shaft is expanded in its region of connection to the implant capsule in such a way that an annular distal end face is formed, which is contacted by the proximal end of the plunger. The distal end face on the outer shaft thus itself also constitutes a sort of plunger, with which the flexible plunger in turn is pressed distally. A clever linking to the aforementioned embodiment is then provided in that the proximal end of the connection ring combining the metal strips of the plunger contacts the distal annular end face of the outer shaft.

The catheter tip preferably has a proximal hollow space. The hollow space preferably surrounds the inner shaft. A hollow space in the proximal region of the catheter tip or at the proximal end of the catheter tip is a simple possibility for designing the catheter tip so as to be axially compressible and at the same time radially expandable. The plunger presses against the proximal end of the hollow space, which is expanded radially and is compressed axially. The radial expansion of the hollow space is forced so to speak by the fixing of the distal region of the catheter tip on the inner shaft.

In this embodiment a hollow space is understood to mean a cavity. Here, the hollow space can be open relative to the inner shaft (half-shell or the like) or can be closed (hollow sphere or the like with an opening for the inner shaft).

FIGS. 1A to 1D show the distal end region of a delivery catheter 1 in a schematic illustration in the form of a longitudinal sectional illustration, more specifically from the distal end of a catheter tip 3, via an implant capsule 5 with implant connector 7, to the distal end region of an outer shaft 9, wherein the course of an inner shaft 11 is also shown schematically in part. The shown delivery catheter 1 is suitable to implant a heart valve prosthesis (not shown) comprising a self-expanding frame and a thereto connected valve. FIG. 1A shows a starting state of the delivery catheter 1, in which the implant capsule 5 is not yet deformed, and FIG. 1B shows the state after the partial release of a prosthesis or an implant and a subsequent resheathing (re-capturing of the implant), which has caused a funnel-shaped expansion of the distal end of the implant capsule to a certain extent. A state of this type would be provided with a catheter according to the prior art.

Figure 2B:
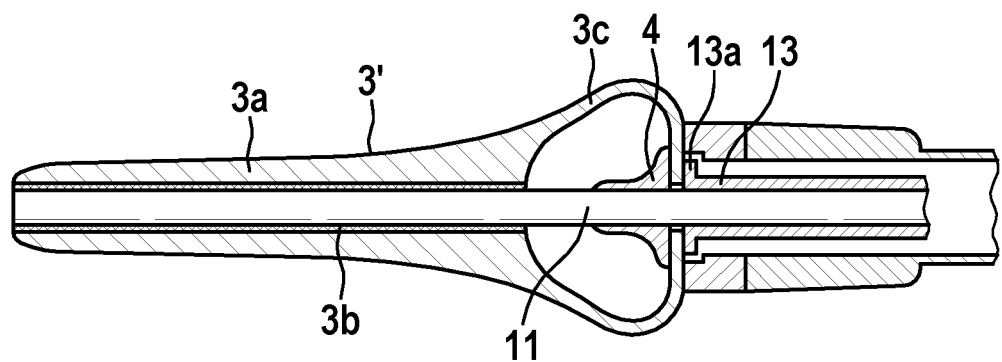

FIGS. 1C and 1D show handling phases of the use of the design according to the invention, wherein reference is made in part to FIGS. 2A and 2B with regard to the components. The outer shaft 9 is moved here distally (to the left in the drawing) during a (further) resheathing process and in so doing pushes forward an elongate plunger 13 by means of the contact between the distal annular end face 9a of the outer shaft and the proximal end of the plunger, which extends substantially over the entire length of the implant capsule 5 (but in FIG. 1A-1D cannot be seen in its entire extent), likewise distally.

The distal end of the plunger, which can be seen in FIGS. 2A and 2B, here contacts the proximal end of the catheter tip 3 (the specific structure of which is illustrated in FIGS. 2A and 2B) and causes a compressive deformation of the tip, which is fixed in its distal end region to the inner shaft and therefore cannot entirely avoid the pressure of the plunger 13 distally. This compressive deformation results in an expansion in the radial direction, which is reversible on account of the material of the catheter tip (resilient expansion). This state of the catheter tip 3 can be seen in FIGS. 1C and 1D. As the outer shaft is advanced further (FIG. 1D), the distal end thereof is deformed/expanded in a funnel-like manner is guided toward the catheter tip 3, which is expanded in the proximal region, whereby on the whole a "flattened", but edge-free contour of the distal end region of the delivery catheter 1 is provided.

In FIGS. 1A-1D, a particular structural design of the implant connector 7 and, coordinated therewith, of the plunger 13 can be seen on the right-hand side, close to the distal end of the outer shaft 9: The implant connector 7 has, in its proximal end portion shaped in the manner of a truncated cone, a plurality of through-holes 7a, through which strips 13a of the plunger 13 cut into strips in that proximal end region are threaded. The strips 13a of the plunger 13 then still run in part proximally concentrically to the longitudinal axis of the catheter and are combined at the proximal end of the plunger with a ring 13b. The ring 13b thus forms a closed proximal end of the plunger 13, which can cooperate with the distal annular end face 9a at the outer shaft 9 in the above-outlined manner. During the displacement of the outer shaft distally and the resultant movement of the plunger in the same direction, the strips 13a of the plunger 13 slide through the through-holes 7a on the implant connector 7.

FIGS. 2A and 2B show the structure of the catheter tip and of the plunger in greater detail in two variants of a catheter tip 3, 3'. The catheter tip 3 has an approximately trumpet-shaped form on the whole and sits on the distal end of the inner shaft 11 of the delivery catheter. It is fixed in its pointed distal end region with an adhesive layer 3b on the inner shaft 11, whereas the expanding, substantially hollow proximal end region 3c is not fixed on the inner shaft.

If the plunger 13 pushes by means of its distal flange portion 13a against the proximal end of the catheter tip 3, this proximal end is displaced distally, and at the same time the proximal end region 3c of the tip is radially expanded. This expansion is reversible.

In the case of the modification shown in FIG. 2B, a plain bushing 4 is joined at the proximal end of the catheter tip 3' and is made from a more rigid plastic material than the catheter tip itself, for example with a Shore hardness of 72 or greater, with a catheter tip with a Shore hardness of 33. The plain bushing 4 on the one hand improves the slidability of the proximal pointed end on the inner shaft 11 and on the other hand improves the introduction of force from the flange portion 13a of the plunger 13 into the proximal end of the catheter tip.

In addition, the invention can also be embodied in a large number of modifications of the examples shown here and aspects of the invention highlighted further above.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A delivery catheter for inserting an implant at a target site in a vessel or organ of a mammal, comprising:
   an inner shaft having an atraumatic distal catheter tip, the inner shaft being configured to carry the implant thereon, the catheter tip having a region that is fixed to the inner shaft and having a region that is deformable and not fixed to the inner shaft;
   an outer shaft surrounding the inner shaft and being displaceable relative thereto;
   an implant capsule at a distal end of the outer shaft configured to encase the implant and to release the implant at the target site via relative displacement of the inner and outer shafts; and
   a plunger axially displaceable with respect to the catheter tip in response to movement of the outer shaft to apply axial compressive force to the catheter tip and deform the region that is deformable and expand that region radially, wherein the catheter tip comprises a soft-resilient moulded plastics part and the region that is deformable is a proximal portion of the soft-resilient moulded plastics part, and the plunger is arranged to contact the proximal portion of the soft-resilient moulded plastics part to axially compress the proximal portion of the soft-resilient moulded plastics part and cause radial expansion of the proximal portion of the soft-resilient moulded plastics part.

2. The delivery catheter according to claim 1, wherein the proximal portion of the soft-resilient moulded plastics part is not fixed to the inner shaft and can be slid relative to the inner shaft during deformation.

3. The delivery catheter according to claim 1, further comprising a bushing within the catheter tip joining a proximal end of the proximal portion of the soft-resilient moulded plastics part to the inner shaft and arranged to transfer axial force from the plunger to the proximal end of the catheter tip, wherein the proximal portion of the soft-resilient moulded plastics part defines a hollow space that expands radially in response to the axial force and is not connected to the inner shaft.

4. The delivery catheter according to claim 1, wherein the region that is fixed comprises a majority of a longitudinal extent of the soft-resilient moulded plastics part and has its entire inner periphery integrally bonded to an outer periphery of the inner shaft.

5. The delivery catheter according to claim 4, wherein a bond between the soft-resilient moulded plastics part and the inner shaft comprises glue or a weld between the entire inner periphery of the region that is fixed and the outer periphery of the inner shaft.

6. The delivery catheter according to claim 1, wherein a diameter of the catheter tip in a non-radially expanded state is substantially equal to the diameter of the implant capsule, and a greatest diameter of the catheter tip in a radially expanded state is in a range between 1.05 times and 1.4 times a diameter of the implant capsule.

7. The delivery catheter according to claim 6, wherein the range is between 1.1 times and 1.35 times.

8. The delivery catheter according to claim 6, wherein the range is between 1.25 times and 1.3 times.

9. The delivery catheter according to claim 1, comprising an implant mounted thereon, wherein the implant is a stent or a heart valve prosthesis.

10. A delivery catheter for inserting an implant at a target site in a vessel or organ of a mammal, comprising:
    an inner shaft having an atraumatic distal catheter tip, the inner shaft being configured to carry the implant thereon, the catheter tip having a region that is fixed to the inner shaft and having a region that is deformable and not fixed to the inner shaft;
    an outer shaft surrounding the inner shaft and being displaceable relative thereto;
    an implant capsule at a distal end of the outer shaft configured to encase the implant and to release the implant at the target site via relative displacement of the inner and outer shafts; and
    a plunger axially displaceable with respect to the catheter tip in response to movement of the outer shaft to apply axial compressive force to the catheter tip and deform the region that is deformable and expand that region radially, wherein the plunger comprises a spirally cut tube in its distal region, and a distal ring flange for forming an area of contact for contacting the catheter tip.

11. The delivery catheter according to claim 10, comprising an implant mounted thereon, wherein the implant is a stent or a heart valve prosthesis.

12. A delivery catheter for inserting an implant at a target site in a vessel or organ of a mammal, comprising:
    an inner shaft having an atraumatic distal catheter tip, the inner shaft being configured to carry the implant thereon, the catheter tip having a region that is fixed to the inner shaft and having a region that is deformable and not fixed to the inner shaft;
    an outer shaft surrounding the inner shaft and being displaceable relative thereto;
    an implant capsule at a distal end of the outer shaft configured to encase the implant and to release the implant at the target site via relative displacement of the inner and outer shafts;
    a plunger axially displaceable with respect to the catheter tip in response to movement of the outer shaft to apply axial compressive force to the catheter tip and deform the region that is deformable and expand that region radially, and an implant connector fixed to the inner shaft inside the implant capsule, the implant connector comprising a guide configured to guide the plunger during axial displacement thereof.

13. The delivery catheter according to claim 12, wherein the guide comprises through-holes and the plunger comprises strips threaded through the through-holes, and a connection ring defines a closed proximal end of the plunger.

14. The delivery catheter according to claim 12, wherein the guide comprises through-holes and the plunger comprises strips threaded through the through-holes, and a connection ring defines a closed proximal end of the plunger, and wherein a proximal end of the connection ring contacts the annular distal end face.

15. The delivery catheter according to claim 12, comprising an implant mounted thereon, wherein the implant is a stent or a heart valve prosthesis.

16. A delivery catheter for inserting an implant at a target site in a vessel or organ of a mammal, comprising:
    an inner shaft having an atraumatic distal catheter tip, the inner shaft being configured to carry the implant thereon, the catheter tip having a region that is fixed to the inner shaft and having a region that is deformable and not fixed to the inner shaft;
    an outer shaft surrounding the inner shaft and being displaceable relative thereto;
    an implant capsule at a distal end of the outer shaft configured to encase the implant and to release the implant at the target site via relative displacement of the inner and outer shafts; and
    a plunger axially displaceable with respect to the catheter tip in response to movement of the outer shaft to apply axial compressive force to the catheter tip and deform the region that is deformable and expand that region radially, wherein the outer shaft comprises an annular distal end face configured for contacting a proximal end of the plunger.

17. The delivery catheter according to claim 16, comprising an implant mounted thereon, wherein the implant is a stent or a heart valve prosthesis.

* * * * *